(12) United States Patent
Medina

(10) Patent No.: US 6,583,161 B1
(45) Date of Patent: Jun. 24, 2003

(54) BENZENESULFONAMIDES AND BENZAMIDES AS THERAPEUTIC AGENTS

(75) Inventor: Julio C. Medina, San Carlos, CA (US)

(73) Assignee: Tularik Inc., SO. San Francisco, CA (US)

( * ) Notice: Subject to any disclaimer, the term of this patent is extended or adjusted under 35 U.S.C. 154(b) by 7 days.

(21) Appl. No.: 09/736,040

(22) Filed: Dec. 12, 2000

Related U.S. Application Data

(63) Continuation of application No. 09/226,703, filed on Jan. 7, 1999, now Pat. No. 6,191,170

(60) Provisional application No. 60/071,137, filed on Jan. 13, 1998.

(51) Int. Cl.$^7$ .............. A61K 31/44; A61K 31/075; A61K 31/505; A61K 31/385; A61K 31/18

(52) U.S. Cl. .............. 514/347; 514/274; 514/302; 514/344; 514/346; 514/347; 514/436; 514/603; 514/604; 514/608; 514/721; 546/116; 546/288; 546/289; 546/295; 544/301; 549/32; 549/365; 564/85; 564/86; 564/89; 564/92; 568/33

(58) Field of Search .............. 546/293, 116, 546/295, 288, 289; 514/346, 302, 344, 347

(56) References Cited

U.S. PATENT DOCUMENTS

| 5,049,695 A | 9/1991 | Abraham et al. ............ 560/27 |
| 5,122,539 A | 6/1992 | Abraham et al. ............ 514/563 |
| 5,290,803 A | 3/1994 | Abraham et al. ............ 514/421 |
| 5,432,191 A | 7/1995 | Abraham et al. ............ 514/421 |
| 5,591,892 A | 1/1997 | Abraham et al. ............ 562/455 |
| 5,756,524 A | 5/1998 | Riordan et al. ............ 514/346 |
| 5,856,484 A | 1/1999 | Breu et al. ............ 544/319 |
| 5,962,682 A | * 10/1999 | Breu et al. ............ 544/123 |

OTHER PUBLICATIONS

Stephan Rover, et al.; "Synthesis and Biochemical Evaluation of N–(4–Phenylthiazol–2–yl)benzenesulfonamides as High–Agginity Inhibitors of Kynurenine 3–Hydroxylase", *J. Med. Chem.*, 1997, vol. 40, No. 26, pp. 4378–4385, especially Scheme 2 on p. 4379.

Chem. Abst. 68:29384.

* cited by examiner

*Primary Examiner*—Peter O'Sullivan
(74) *Attorney, Agent, or Firm*—Townsend and Townsend and Crew LLP

(57) ABSTRACT

The invention provides compounds, compositions and methods relating to novel aromatic derivatives and their use as pharmacologically active agents. The compositions find particular use as pharmacological agents in the treatment of disease states, particularly cancer, psoriasis, vascular restenosis, infections, atherosclerosis and hypercholesterolemia, or as lead compounds for the development of such agents.

50 Claims, 1 Drawing Sheet

BENZENESULFONAMIDES AND BENZAMIDES AS THERAPEUTIC AGENTS

CROSS-REFERENCES TO RELATED APPLICATIONS

This applications is a continuation of U.S. Ser. No. 09/226,703, filed Jan 7, 1999, now U.S. Pat No. 6,191,170, which claims the benefit of U. S. Provisional Application No. 60/071,137, filed Jan. 13, 1998, the disclosures of each being incorporated by reference.

STATEMENT REGARDING FEDERALLY SPONSORED RESEARCH

The invention described herein was not made with the aid of any federally sponsored grants.

FIELD OF THE INVENTION

The field of the invention is benzenesulfonamides or benzamides and their use as pharmacologically active agents capable of regulating low-density lipoprotein (LDL) receptor expression and of inhibiting abnormal cell proliferation.

BACKGROUND OF THE INVENTION

Atherosclerosis is a leading cause of death in the United States. The disease results from excess cholesterol accumulation in the arterial walls, which forms plaques that inhibit blood flow and promote clot formation, ultimately causing heart attacks, stroke and claudication. A principal source of these cholesterol deposits is the low-density lipoprotein (LDL) particles that are present in the blood. There is a direct correlation between LDL concentration and plaque formation in the arteries. LDL concentration is itself largely regulated by the supply of active LDL cell surface receptors, which bind LDL particles and translocate them from the blood into the cell's interior. Accordingly, the upregulation of LDL receptor expression provides an important therapeutic target.

Lipoprotein disorders have been previously called the hyperlipoproteinemias and defined as the elevation of a lipoprotein level above normal. The hyperlipoproteinemias result in elevations of cholesterol, triglycerides or both, and are clinically important because of their contribution to atherosclerotic diseases and pancreatitis.

Lipoproteins are spherical macromolecular complexes of lipid and protein. The lipid constituents of lipoproteins are esterified and unesterified (free) cholesterol, triglycerides, and phospholipids. Lipoproteins transport cholesterol and triglycerides from sites of absorption and synthesis to sites of utilization. Cholesteryl esters and triglycerides are nonpolar and constitute the hydrophobic core of lipoproteins in varying proportions. The lipoprotein surface coat contains the polar constituents—free cholesterol, phospholipids, and apolipoproteins—that permit these particles to be miscible in plasma.

Cholesterol is used for the synthesis of bile acids in the liver, the manufacture and repair of cell membranes, and the synthesis of steroid hormones. There are both exogenous and endogenous sources of cholesterol. The average American consumes about 400 mg of cholesterol each day and produces an additional 560 to 1,000 mg in the liver and other tissues. Another source is the 500 to 1,000 mg of biliary cholesterol that is secreted into the intestine daily; about 50 percent is reabsorbed (enterohepatic circulation). The rate-limiting enzyme in endogenous cholesterol synthesis is 3-hydroxy-3-methylglutaryl coenzyme A (HMG-CoA) reductase. Triglycerides, which are nonpolar lipids consisting of a glycerol backbone and three fatty acids of varying length and degrees of saturation, are used for storage in adipose tissue and for energy.

Lipoproteins are classified into groups based upon size, density, electrophoretic mobility, and lipid and protein composition. Very low density lipoproteins (VLDL) are large, triglyceride-rich lipoproteins that are synthesized and secreted by hepatocytes. VLDL interacts with lipoprotein lipase in capillary endothelium, and the core triglycerides are hydrolyzed to provide fatty acids to adipose and muscle tissue. About half of the catabolized VLDL particles are taken up by hepatic LDL receptors and the other half remain in plasma, becoming intermediate-density lipoprotein (IDL). IDL is enriched in cholesteryl esters relative to triglycerides and is gradually converted by hepatic triglyceride lipase to the smaller, denser, cholesterol ester-rich LDL. As IDL is converted to LDL, apolipoprotein E becomes detached, and only one apolipoprotein remains, apo B-100.

LDL normally carries about 75 percent of the circulating cholesterol. Cellular LDL uptake is mediated by a glycoprotein receptor molecule that binds to apo B-100. Approximately 70 percent of LDL is cleared by receptor uptake, and the remainder is removed by a scavenger cell pathway using nonreceptor mechanisms. The LDL receptors span the thickness of the cell's plasma membrane and are clustered in specialized regions where the cell membrane is indented to form craters called coated pits. These pits invaginate to form coated vesicles, where LDL is separated from the receptor and delivered to a lysosome so that digestive enzymes can expose the cholesteryl ester and cleave the ester bond to form free cholesterol. The receptor is recycled to the cell surface.

As free cholesterol liberated from LDL accumulates within cells, there are three important metabolic consequences. First, there is a decrease in the synthesis of HMG-CoA reductase, the enzyme that controls the rate of de novo cholesterol biosynthesis by the cell. Second, there is activation of the enzyme acyl cholesterol acyltransferase (ACAT), which esterifies free cholesterol into cholesterol ester, the cell's storage form of cholesterol. Third, accumulation of cholesterol suppresses the cell's synthesis of new LDL receptors. This feedback mechanism reduces the cell's uptake of LDL from the circulation.

Lipoproteins play a central role in atherosclerosis. This association with the most common cause of death in the developed world defines the principal clinical importance of the hyperlipoproteinemias. Individuals with an elevated cholesterol level are at higher risk for atherosclerosis. Multiple lines of evidence, including epidemiological, autopsy, animal studies and clinical trials, have established that LDL is atherosclerogenic and that the higher the LDL level, the greater the risk of atherosclerosis and its clinical manifestations. A certain degree of LDL elevation appears to be a necessary factor in the development of atherosclerosis, although the process is modified by many other factors (e.g., blood pressure, tobacco use, blood glucose level, antioxidant level, and clotting factors). Acute pancreatitis is another major clinical manifestation of dyslipoproteinemia. It is associated with chylomicronemia and elevated VLDL levels. Most patients with acute pancreatitis have triglyceride levels above 2,000 mg/dL, but a 1983 NIH consensus development conference recommended that prophylactic treatment of hypertriglyceridemia should begin when fasting levels exceed 500 mg/dL. The mechanism by which chylomicronemia and elevated VLDL levels cause pancreatitis is unclear. Pancreatic lipase may act on triglycerides in pancreatic capillaries, resulting in the formation of toxic fatty acids that cause inflammation.

Abundant evidence indicates that treatment of hyperlipoproteinemia will diminish or prevent atherosclerotic complications. In addition to a diet that maintains a normal body weight and minimizes concentrations of lipids in plasma, therapeutic agents that lower plasma concentrations of lipoproteins, either by diminishing the production of lipoproteins or by enhancing the efficiency of their removal from plasma, are clinically important.

The most promising class of drugs currently available for the treatment of hyperlipoproteinemia or hypercholesterolemia acts by inhibiting HMG-CoA reductase, the rate-limiting enzyme in endogenous cholesterol synthesis. Drugs of this class competitively inhibit the activity of the enzyme. Eventually, this inhibition leads to a decrease in the endogenous synthesis of cholesterol and by normal homeostatic mechanisms, plasma cholesterol is taken up by LDL receptors to restore the intracellular cholesterol balance.

Through both the release of precursors of LDL and receptor-mediated LDL uptake from the serum, liver cells play a critical role in maintaining serum cholesterol homeostasis. In both man and animal models, an inverse correlation appears to exist between liver LDL receptor expression levels and LDL-associated serum cholesterol levels. In general, higher hepatocyte LDL receptor numbers result in lower LDL-associated serum cholesterol levels. Cholesterol released into hepatocytes can be stored as cholesteryl esters, converted into bile acids and released into the bile duct, or it can enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element (SRE), appears to confer this sterol end product repression. This element has been extensively investigated (Brown, Goldstein and Russell, U.S. Pat. Nos. 4,745,060 and 4,935,363). The SRE can be inserted into genes that normally do not respond to cholesterol, conferring sterol end product repression of the chimeric gene. The exact mechanism of the repression is not understood. Brown and Goldstein have disclosed methods for employing the SRE in a screen for drugs capable of stimulating cells to synthesize LDL receptors (U.S. Pat. No. 4,935,363). It would be most desirable if the synthesis of LDL receptors could be upregulated at the level of gene expression. The upregulation of LDL receptor synthesis at this level offers the promise of resetting the level of serum cholesterol at a lower, and clinically more desirable, level. Presently, however, there are no cholesterol lowering drugs that are known to operate at the level of gene expression. The present invention describes methods and compounds that act to inhibit directly or indirectly the repression of the LDL receptor gene, resulting in induction of the LDL receptor on the surface of liver cells, facilitating LDL uptake, bile acid synthesis and secretion to remove cholesterol metabolites and hence the lowering of LDL-associated serum cholesterol levels.

A number of human diseases stem from processes of uncontrolled or abnormal cellular proliferation. Most prevalent among these is cancer, a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells even after prolonged exposure to the drug. Unfortunately, none of the current chemotherapies possess an ideal profile. Most possess very narrow therapeutic indexes, and in practically every instance cancerous cells exposed to slightly sublethal concentrations of a chemotherapeutic agent will develop resistance to such an agent, and quite often cross-resistance to several other antineoplastic agents.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

What is needed in the art are new methods and compounds which act to inhibit directly or indirectly the repression of the LDL receptor gene. The compounds should also result in the induction of the LDL receptor on the surface of liver cells, facilitating LDL uptake, bile acid synthesis and secretion to remove cholesterol metabolites and thereby lower LDL-associated serum cholesterol levels.

SUMMARY OF THE INVENTION

The invention provides novel benzenesulfonamide, benzamide, diarylsulfone and benzophenone compounds and compositions, and methods for their use as diagnostic and pharmacologically active agents.

Compounds of the present invention which are useful in the compositions and methods described herein have the formula:

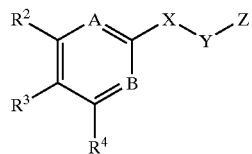

in which the letter A represents N or C—$R^1$; the letter B represents N or C—$R^5$; and $R^1$ and $R^5$ independently represent hydrogen, halogen, ($C_1$–$C_8$)alkyl, ($C_1$–$C_8$) heteroalkyl, —$OR^6$, —$NR^6R^7$, —$S(O)_mR^6$, —CN, —$NO_2$, —$S(O)_nNR^6R^7$, or —$N_3$; wherein $R^6$ and $R^7$ are independently selected from hydrogen, ($C_1$–$C_8$)alkyl, and ($C_1$–$C_8$) heteroalkyl; m is an integer of from 0 to 3; and n is an integer of from 1 to 2.

The symbols $R^2$ and $R^3$ are independently —$OR^8$, —$SR^8$ and —$NR^8R^9$, wherein $R^8$ and $R^9$ are independently hydrogen, ($C_1$–$C_6$)alkyl or ($C_1$–$C_6$)heteroalkyl. The symbol $R^4$ represents hydrogen, ($C_1$–$C_8$)alkyl, ($C_1$–$C_8$)heteroalkyl, —$OR^{10}$, —$SR^{10}$ or —$NR^{10}R^{11}$, wherein $R^{10}$ and $R^{11}$ are independently selected from hydrogen, ($C_1$–$C_6$)alkyl or ($C_1$–$C_6$)heteroalkyl.

Optionally, $R^1$ is linked to $R^2$ to form a fused ring, $R^2$ is linked to $R^3$ to form a fused ring, or $R^2$ is linked to both of $R^1$ and $R^3$ to form two additional fused rings.

The letter X represents —$S(O)_p$— or —C(O)—, wherein p is 1 or 2. The letter Y represents a single bond, —$CH_2$— or —$N(R^{12})$—, wherein $R^{12}$ is selected from hydrogen, ($C_1$–$C_6$)alkyl, ($C_1$–$C_6$)heteroalkyl and arylalkyl; and the letter Z represents an aryl group or an arylalkyl group.

The compositions find particular use as pharmacological agents in the treatment of disease states, particularly hyperlipoproteinemias and those disease states resulting from abnormal cell proliferation, or as lead compounds for the development of such agents. The invention further provides novel methods for treating hyperlipoproteinemias or proliferative disorders by administering to a patient an effective formulation of one or more of the subject compositions.

Other objects, features and advantages will become apparent to those skilled in the art from the following description and claims.

DETAILED DESCRIPTION OF THE INVENTION

Abbreviations and Definitions

Figure 1:
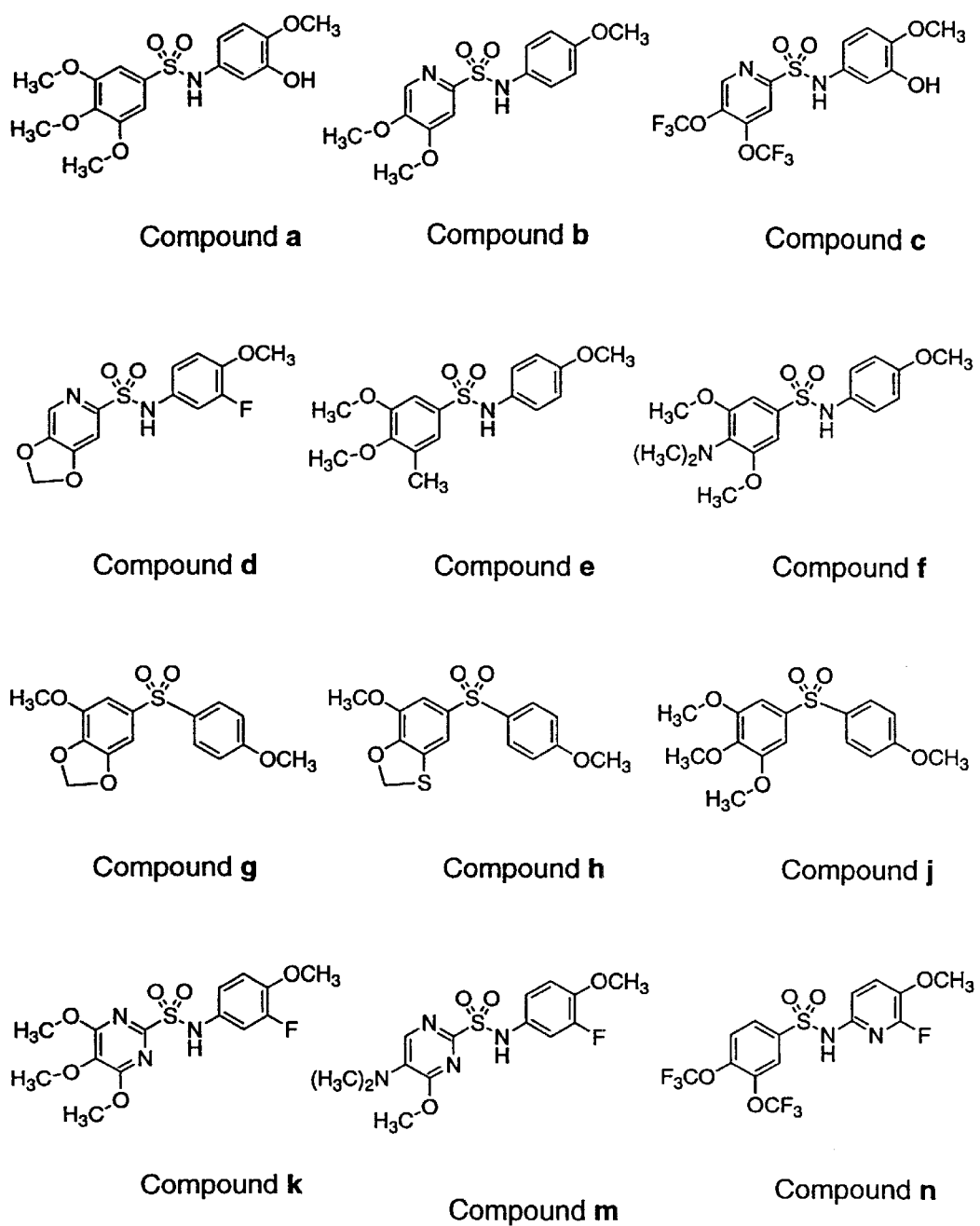
FIG. 1 provides exemplary structures of compounds of the present invention.

The term "alkyl," by itself or as part of another substituent, means, unless otherwise stated, a straight or branched chain, cyclic or hybrid hydrocarbon radical, which may be fully saturated, mono- or polyunsaturated and can include di- and multi-radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." Typically, an alkyl group will have from 1 to 24 carbon atoms, with those groups having 10 or fewer carbon atoms being preferred in the present invention. The term "alkylene" by itself or as part of another substituent means a divalent radical derived from an alkane, as exemplified by —$CH_2CH_2CH_2CH_2$—. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, cyclic or hybrid hydrocarbon radical consisting of the stated number of carbon atoms and from one to three heteroatoms selected from the group consisting of O, N, Si and S, and wherein the nitrogen and sulfur atoms may optionally be oxidized and the nitrogen heteroatom may optionally be quarternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—$S(O)_2CH_3$, —CH=CH—O—$CH_3$, —Si($CH_3$)$_3$, —$Ch_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. Also included in the term "heteroalkyl" are those radicals described in more detail below as "heterocycloalkyl."

The terms "cycloalkyl" and "heterocycloalkyl", by themselves or in combination with other terms, represent, unless otherwise stated, cyclic versions of "alkyl" and "heteroalkyl", respectively. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quartenized. Non-limiting examples of aryl groups include phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkenyl, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halo, —SiR'R"R''', —OC(O)R', —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R''' each independently refer to a hydrogen or an unsubstituted($C_1$–$C_{10}$)alkyl group.

Similarly, substituents for the aryl groups are varied and are selected from: -halo, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R' and R" are independently selected from hydrogen, ($C_1$–$C_8$)alkyl, aryl, aryl-($C_1$–$C_4$)alkyl, and aryloxy-($C_1$–$C_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 1 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Embodiments of the Invention

The present invention provides compounds and compositions which are useful in therapeutic applications. In particular, the compounds are useful in the diagnosis and treatment of lipoprotein disorders. The compounds are also useful in reducing cell proliferation, particularly abnormal cell proliferation. Additionally, the compounds are useful in drug screens for the evaluation of other therapeutic agents directed to hyperlipoproteinemias and neoplasia. Recently, pentafluorosulfonamide compounds have been described which can regulate low-density lipoprotein (LDL) receptor expression (see Co-pending applications U.S. Ser. No. 08/896,827 filed Jul. 18, 1997 and U.S. Ser. No. 08/917,025, filed Aug. 22, 1997). It is believed that the pentafluorosulfonamides are effective due to a covalent modification of a target protein, wherein covalent attachment takes place on the electron-poor pentafluorophenyl (or polyhalogenated phenyl) ring by displacement of a para-fluoro atom. Accordingly, it was quite surprising that the compounds and compositions described herein, which have an electron-rich aromatic ring and generally do not form a covalent bond with their target protein, are similarly effective at regulating LDL receptor expression and inhibiting abnormal cell proliferation.

Compounds

In one aspect, the present invention provides compounds of general formula:

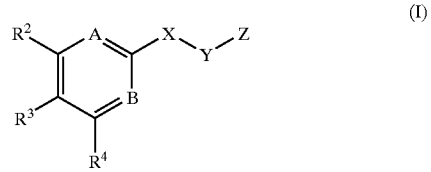

(I)

In formula (I), the letter A represents N or C—$R^1$ and the letter B represents N or C—$R^5$. $R^1$ and $R^5$ independently represent hydrogen, halogen, $(C_1-C_8)$alkyl, $(C_1-C_8)$ heteroalkyl, —$OR^6$, —$NR^6R^7$, —$S(O)_mR^6$, —CN, —$NO_2$, $S(O)_nNR^6R^7$, or —$N_3$; wherein $R^6$ and $R^7$ are independently selected from hydrogen, $(C_1-C_8)$alkyl, and $(C_1-C_8)$ heteroalkyl; m is an integer of from 0 to 3; and n is an integer of from 1 to 2. Preferred groups for $R^1$ and $R^5$ are hydrogen, unsubstituted$(C_1-C_8)$alkyl, —$OR^6$, —$NR^6R^7$, and —$SR^6$. In preferred embodiments, A is C—H or N and B is C—H or N.

The symbols $R^2$ and $R^3$ are independently —$OR^8$, —$SR^8$ and —$NR^8R^9$, wherein $R^8$ and $R^9$ are independently hydrogen, $(C_1-C_6)$alkyl or $(C_1-C_6)$heteroalkyl. In preferred embodiments, $R^2$ and $R^3$ are independently —$OR^8$, —$SR^8$ or —$NR^8R^9$, wherein $R^8$ and $R^9$ are independently hydrogen or $(C_1-C_3)$alkyl. More preferably, $R^2$ and $R^3$ are independently methoxy, ethoxy, propoxy, isopropoxy, trifluoromethoxy, methylthio, ethylthio, propylthio or isopropylthio.

The symbol $R^4$ represents hydrogen, $(C_1-C_8)$alkyl, $(C_1-C_8)$heteroalkyl, —$OR^{10}$, —$SR^{10}$ or —$NR^{10}R^{11}$, wherein $R^{10}$ and $R^{11}$ are independently selected from hydrogen, $(C_1-C_6)$alkyl or $(C_1-C_6)$heteroalkyl. Preferably, $R^4$ represents hydrogen, $(C_1-C_4)$alkyl, —$OR^{10}$, or —$SR^{10}$, wherein $R^{10}$ is hydrogen or $(C_1-C_3)$alkyl.

Optionally, $R^1$ is linked to $R^2$ to form a fused ring, $R^2$ is linked to $R^3$ to form a fused ring, or $R^2$ is linked to both of $R^1$ and $R^3$ to form two additional fused rings. Preferably, $R^2$ and $R^3$ are combined together to form a group selected from $(C_1-C_4)$alkylene, $(C_1-C_4)$heteroalkylene, $(C_2-C_4)$ alkenylene and $(C_2-C_4)$heteroalkenylene. More preferably, $R^2$ and $R^3$, when taken together, form a group selected from —$OCH_2O$—, —$OCH_2S$—, —$OCH_2CH_2O$—, —$OCH_2CH_2S$—, —NH—C(O)—NH—, —NH—CH=NH— and —$CH_2CH_2CH_2$—.

The letter X represents —$S(O)_p$— or —C(O)—, wherein p is 1 or 2. Preferably, X is —$S(O)_2$—. The letter Y represents a single bond, —$CH_2$— or —$N(R^{12})$—, wherein $R^{12}$ is selected from hydrogen, $(C_1-C_6)$alkyl, $(C_1-C_6)$ heteroalkyl and arylalkyl. In preferred embodiments, Y is —$N(R^{12})$—, wherein $R^{12}$ is hydrogen, unsubstituted $(C_1-C_3)$alkyl or hydroxy-substituted $(C_2-C_5)$alkyl.

The letter Z represents an aryl group or an arylalkyl group. Preferably, Z is a substituted aryl or arylalkyl group. More preferably Z is a phenyl, pyridyl or naphthyl moiety which is substituted with one or more fluoro, hydroxy or methoxy groups. Most preferred are compounds in which Z represents a 4-methoxyphenyl, 3-hydroxy-4-methoxyphenyl, 3-fluoro-4-methoxyphenyl, 4-aminophenyl, 4-dimethylaminophenyl, or 6-fluoro-5-methoxy-2-pyridyl group.

In one group of preferred embodiments, A is C—$R^1$, B is C—$R^5$, in which $R^1$ and $R^5$ are independently hydrogen or $(C_1-C_3)$alkyl, X is —$S(O)_2$—, Y is —$N(R^{12})$—, and Z is a phenyl group or a naphthyl group. More preferably, Y is —NH— and Z is a substituted phenyl group. In particularly preferred embodiments, A is C—H, B is C—H, $R^2$ is —$OR^8$, $R^3$ is —$OR^8$, $R^4$ is hydrogen or —$OR^{10}$, X is —$S(O)_2$—, Y is —NH—, and Z is a substituted phenyl group. Most preferred are those embodiments in which A is C—H, B is C—H, $R^2$ is —$OR^8$, $R^3$ is —$OR^8$, $R^4$ is hydrogen or —$OR^{10}$, X is —$S(O)_2$—, Y is —NH—, and Z is a substituted phenyl group represented by

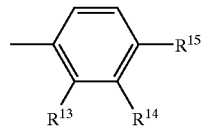

wherein $R^{13}$, $R^{14}$ and $R^{15}$ are each independently selected from hydrogen, halogen, $(C_1-C_6)$alkyl, $(C_1-C_6)$heteroalkyl, —$OR^{16}$, —$NR^{16}R^{17}$, —CN, —$NO_2$, wherein $R^{16}$ and $R^{17}$ are independently selected from hydrogen, $(C_1-C_6)$alkyl and $(C_1-C_6)$heteroalkyl, or when attached to the same nitrogen atom are combined to form a 5-, 6- or 7-membered ring. Within this group of embodiments, $R^{13}$ is preferably hydrogen, and $R^{14}$ and $R^{15}$ are other than hydrogen.

In other particularly preferred embodiments, A is C—H, B is C—H, $R^2$ and $R^3$ taken together are —$OCH_2O$—, $R^4$ is —$OR^{10}$, X is —$S(O)_2$—, Y is —$N(R^{12})$—, and Z is a substituted phenyl group. As above, the most preferred embodiments are those in which A is C—H, B is C—H, $R^2$ and $R^3$ taken together are —$OCH_2O$—, $R^4$ is —$OR^{10}$, X is —$S(O)_2$—, Y is —$N(R^{12})$—, and Z is a substituted phenyl group represented by

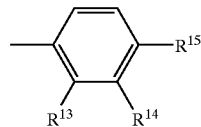

wherein $R^{13}$, $R^{14}$ and $R^{15}$ are each independently selected from hydrogen, halogen, $(C_1-C_6)$alkyl, $(C_1-C_6)$heteroalkyl, —$OR^{16}$, —$NR^{16}R^{17}$, —CN, —$NO_2$, wherein $R^{16}$ and $R^{17}$ are independently selected from hydrogen, $(C_1-C_6)$alkyl and $(C_1-C_6)$heteroalkyl, or when attached to the same nitrogen atom are combined to form a 5-, 6- or 7-membered ring. Within this group of embodiments, $R^{13}$ is preferably hydrogen, and $R^{14}$ and $R^{15}$ are other than hydrogen.

In another group of preferred embodiments, A is C—H, B is C—H, $R^2$ and $R^3$ are independently selected from methoxy, difluoromethoxy and trifluoromethoxy, $R^4$ is a member selected from hydrogen, methoxy, difluoromethoxy and trifluoromethoxy, X is —$S(O)_2$—, Y is —NH—, and Z is phenyl substituted by one or more fluoro, methoxy, or hydroxy groups.

In yet another group of preferred embodiments, A is C—H, B is C—H, $R^2$ and $R^3$ are independently selected from methoxy, difluoromethoxy and trifluoromethoxy, $R^4$ is selected from hydrogen, methoxy, difluoromethoxy and trifluoromethoxy, X is —S(O)$_2$—, Y is —NH—, and Z is selected from 4-dimethylaminophenyl, 4-aminophenyl, 4-methoxyphenyl, 3-fluoro-4-methoxyphenyl and 3-hydroxy-4-methoxyphenyl.

In still another group of preferred embodiments, A is C—H, B is C—H, $R^2$, $R^3$ and $R^4$ are each methoxy, X is —S(O)$_2$—, Y is —NH—, and Z is selected from 4-dimethylaminophenyl, 4-aminophenyl, 4-methoxyphenyl, 3-fluoro-4-methoxyphenyl and 3-hydroxy-4-methoxyphenyl.

In yet another group of preferred embodiments, A is C—OCH$_3$, B is C—H, $R^2$ and $R^3$ are each methoxy, $R^4$ is hydrogen, X is —S(O)$_2$—, Y is —NH—, and Z is selected from 4-dimethylaminophenyl, 4-aminophenyl, 4-methoxyphenyl, 3-fluoro-4-methoxyphenyl and 3-hydroxy-4-methoxyphenyl.

Structures of exemplary sulfonamides and diarylsulfones of the present invention are depicted in FIG. 1.

Preparation of Compounds

The compounds of the present invention can be prepared using standard synthetic methods and commercially available starting materials.

In one general embodiment, the methods involve combining an appropriate sulfonyl chloride (iii) with an appropriate aniline (iv), as outlined in Scheme 1 (for embodiments in which A is C—$R^1$ and B is C—$R^5$), to yield a sulfonamide (v). The necessary sulfonyl chlorides (iii) can be prepared by sulfonation of the appropriately substituted aromatic compounds (i) with fuming sulfuric acid, followed by treatment with a chlorinating agent, such as PCl$_5$, POCl$_3$ and the like, to afford the corresponding sulfonyl chlorides (iii), (Scheme 1). When the sulfonamides contain certain groups, such as chloro or bromo, these groups can be catalytically reduced to produce yet other analogous sulfonamides (vi).

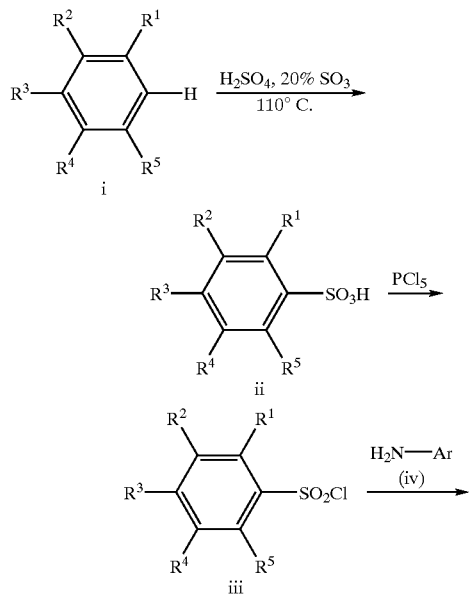

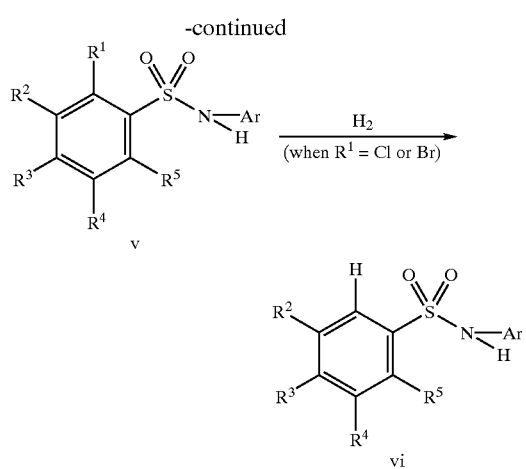

An alternative method of preparing the desired sulfonyl chlorides (iii) is by heating the starting aromatic compounds (i) with chlorosulfonic acid as shown in Scheme 2.

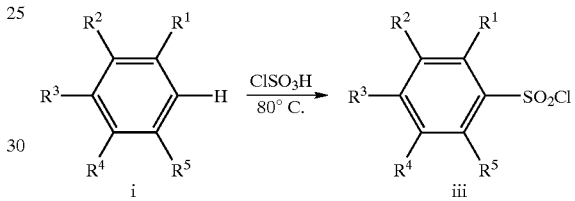

Still further, the desired sulfonyl chlorides (iii) can be prepared from the corresponding anilines (vii) by dissolving the aniline in an acidic aqueous solution, such as HCl and the like, followed by addition of an aqueous solution of sodium nitrite at a temperature below ambient temperature, typically between −20 and +5° C. The resulting mixture, containing the desired diazonium salt, is then added to a saturated solution of sulfur dioxide in glacial acetic acid containing cuprous chloride, at a temperature between −10 and +10° C., to yield the corresponding sulfonyl chloride (iii) (see Scheme 3).

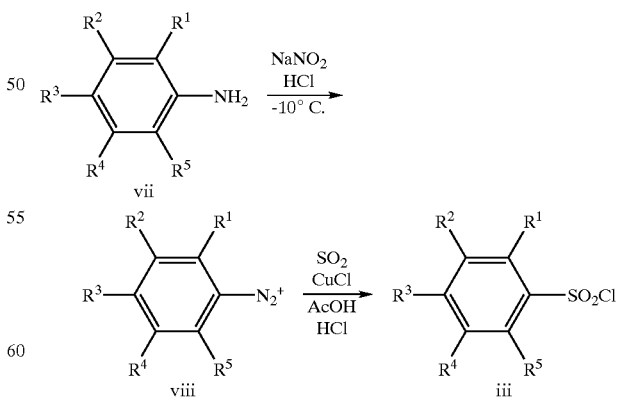

Sulfonyl chlorides (iii) useful in preparation of sulfonamides described herein can also be prepared by oxidation of the respective thiophenols (ix) with chlorine and hydrogen peroxide in acetic acid as shown in Scheme 4.

Scheme 4

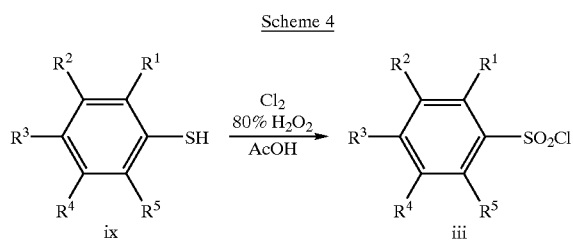

The sulphinamides described herein can be synthesized by reaction of suitably substituted sulphinyl chlorides (xiii) with the appropriate amine (iv), as shown in Scheme 5. The necessary sulphinyl chlorides (xiii) are prepared by metal-halogen exchange reaction on the appropriate aryl bromides (x), chlorides or iodides, with an alkyllithium reagent such as butyl-lithium, or with magnesium metal, followed by treatment of the resulting aryl organometallic compounds (xi) with sulfur dioxide affords the lithium sulfinates (xii) that can be further reacted with thionyl chloride to afford the desired sulphinyl chlorides (xiii).

Scheme 5

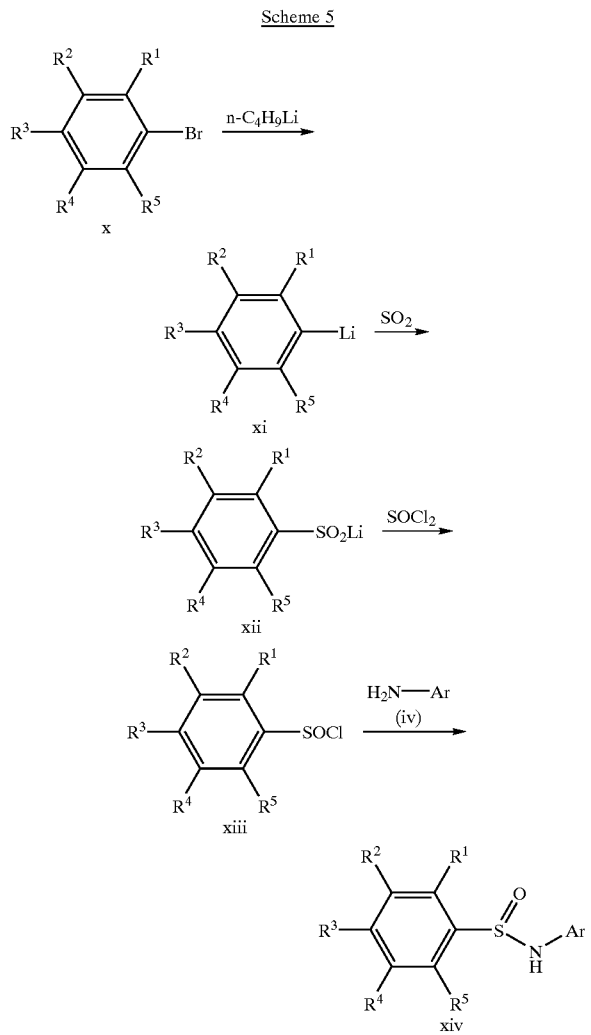

The sulfoxides (xviii) and sulfones (xix) described herein can be prepared by reaction of the desired substituted thiophenols (xv) with the derivatized benzylic halides (xvi) to yield the corresponding sulfides (xvii), which can be oxidized to the corresponding sulfoxides (xviii) or sulfones according to Scheme 6. The necessary thiophenols (xv) can be prepared from the starting substituted anilines (vii) by diazotization, followed by treatment with sodium sulfide (Scheme 6).

Alternatively, the thiophenols (xv) can be prepared by treatment of the diazonium salts (viii) with potassium ethyl xanthate, followed by saponification of the resulting xanthates (xx), as shown in Scheme 7. Other alternate methods for the synthesis of the desired substituted thiophenols (xv) are described in the chemical literature and should be well known to individuals versed in the art of organic synthesis.

Scheme 6

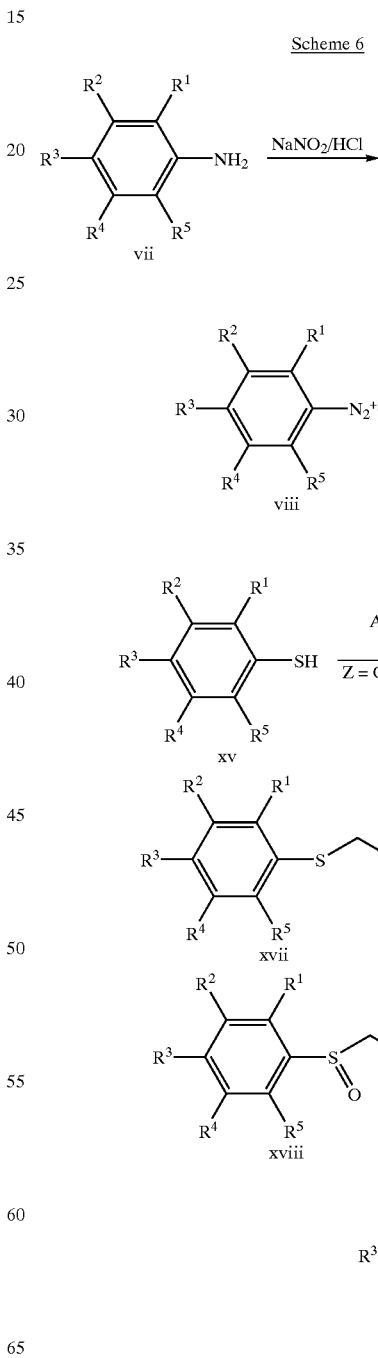

Scheme 7

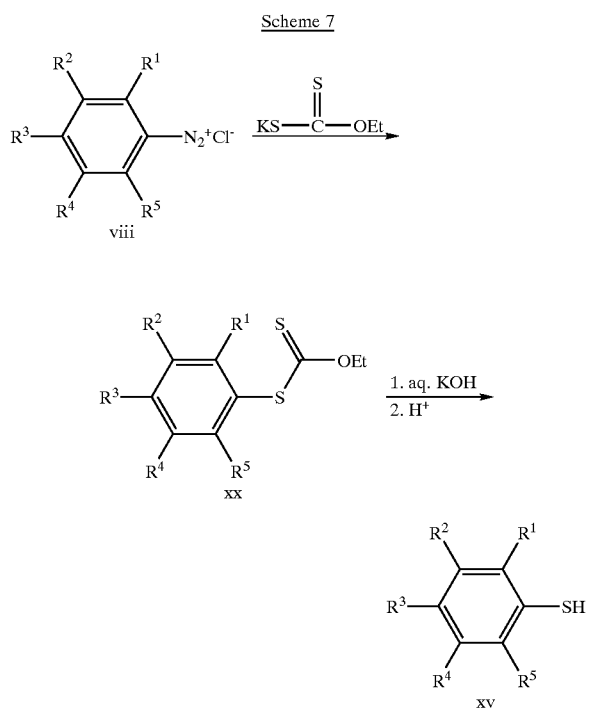

In a similar manner, diarylsulfoxides and sulfones can be prepared beginning with an appropriately substituted thiophenol (xv). Treatment of the thiophenol with strong base and addition of the resultant thiophenoxide ion to a diazonium salt (xx) provides the diaryl sulfide (xxi). Oxidation with MCPBA and/or hydrogen peroxide can provide the desired diarylsulfoxides or diarylsulfones (see Scheme 8).

Scheme 8

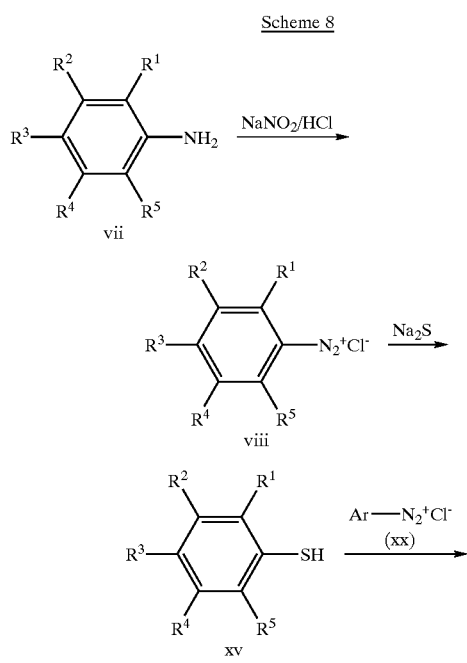

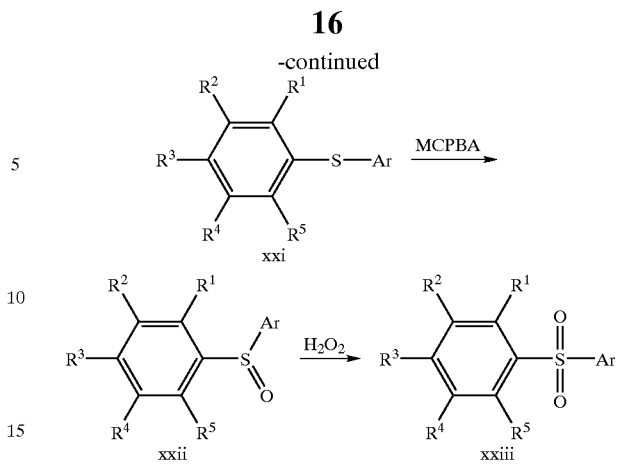

Occasionally, the starting materials for the above transformations will contain functional groups (e.g., amino, hydroxy, carboxy, thiol) which are not immediately compatible with the conditions of the given reaction. In such cases, these groups can be protected with suitable protecting groups which can be removed subsequent to the transformation to give the original functionality. Suitable protecting groups and procedures are provided in Greene, et al., Protective Groups In Organic Synthesis, 2nd Ed., John Wiley & Sons, Inc., 1991.

Analysis of Compounds

The subject compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically regulating LDL receptor gene expression. Compounds may be evaluated in vitro for their ability to increase LDL receptor expression using western-blot analysis, for example, as described in Tam et al. (*J. Biol. Chem.* 1991, 266, 16764). Established animal models to evaluate hypocholesterolemic effects of compounds are known in the art. For example, compounds disclosed herein are shown to lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med. Chem.* 1995, 38, 277).

Certain preferred compounds and compositions display specific toxicity to various types of cells. Certain compounds and compositions of the present invention exert their cytotoxic effects by interacting with cellular tubulin. For certain preferred compounds and compositions of the present invention, that interaction can be covalent and irreversible. Compounds and compositions may be evaluated in vitro for their ability to inhibit cell growth, for example, as described in Ahmed et al. (*J. Immunol. Methods* 1994, 170, 211). Established animal models to evaluate antiproliferative effects of compounds are known in the art. For example, compounds can be evaluated for their ability to inhibit the growth of human tumors grafted into immunodeficient mice using methodology similar to that described by Rygaard and Povlsen (*Acta Pathol. Microbiol. Scand.* 1969, 77, 758) and Giovanella and Fogh (*Adv. Cancer Res.* 1985, 44, 69).

Formulation and Administration of Compounds and Pharmaceutical Compositions

The invention provides methods of using the subject compounds and compositions to treat disease or provide medicinal prophylaxis, to upregulate LDL receptor gene expression in a cell, to reduce blood cholesterol concentration in a host, to slow down and/or reduce the growth of tumors, etc. These methods generally involve contacting the cell with or administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically or chemically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic or antiproliferative therapeutic or prophylactic agents, different from the subject compounds. In many instances, administration in conjunction with the subject compositions enhances the efficacy of such agents. Examplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as gemfibrozil, clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES

General

$^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett-Packard 5989A mass spectrometer. Mass spectrometry results are reported as the ratio of mass over charge, followed by the relative abundance of each ion (in parentheses).

Starting materials for the synthesis of the examples of the present invention are available from commercial sources or are known compounds described in the published literature.

For example, starting sulfonyl chlorides can be prepared as follows:

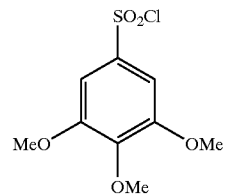

3,4,5-Trimethoxybenzenesulfonyl Chloride 3,4,5-Trimethoxybenzenesulfonyl chloride was synthesized from 3,4,5-trimethoxyaniline according to the procedure described in G. Pifferi and R. Monguzzi, *Journal of Pharmaceutical Sciences*, 1973, 62, 1393. In this procedure the aniline was dissolved in concentrated hydrochloric acid and to the resulting mixture was added a solution of aqueous sodium nitrite at 0° C., the resulting mixture containing the desired diazonium salt was added at 5° C. to a saturated solution of sulfur dioxide in glacial acetic acid containing substoichiometric amount of cuprous chloride. The mixture was stirred at ambient temperature for 3 h, poured into cold water, and the product extracted with dichloromethane. The solvent was evaporated and the solid residue was recrystallized from hexanes.

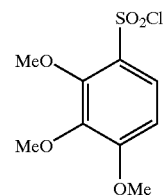

2,3,4-Trimethoxybenzenesulfonyl Chloride 2,3,4-Trimethoxybenzenesulfonyl chloride is synthesized by reaction of pyrogallol trimethyl ether with chlorosulfonic acid in chloroform at 0° C. according to the procedure described in G. Pifferi and R. Monguzzi, *Journal of Pharmaceutical Sciences*, 1973, 62, 1393.

Example 1

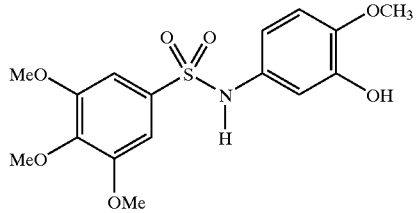

1-[(3-Hydroxy-4-methoxyphenyl)aminosulfonyl]-3,4,5-trimethoxybenzene

To a solution of 3,4,5-trimethoxybenzenesulfonyl chloride (500 mg, 1.88 mmol) in methanol (10 mL) was added 3-hydroxy-4-methoxyaniline (523 mg, 3.76 mmol) at ambient temperature. After stirring for 1 h, the reaction mixture was concentrated and the crude residue was purified by chromatography over silica to afford 430 mg (62%) of product as fine white needles, m.p. 145–146° C. $^1$H-NMR (CDCl$_3$): δ9.74 (1H, s), 9.15 (1H, s), 6.98 (2H, s), 6.78 (1H, d, J=8.8 Hz), 6.63 (1H, d, J=2.6 Hz), 6.50 (1H, dd, J=8.8, 2.6 Hz), 3,76 (6H, s), 3.70 (3H, s), 3.68 (3H, s). Anal. Calcd. for C$_{16}$H$_{19}$N$_1$O$_7$S: C, 52.03; H, 5.18; N, 3.79; S, 8.68. Found: C, 51.87; H, 5.28; N, 3.76; S, 8.77.

Example 2

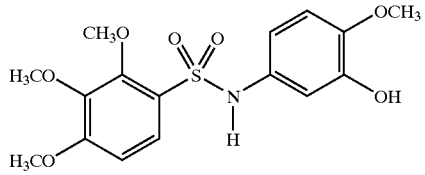

1-[(3-Hydroxy-4-methoxyphenyl)aminosulfonyl]-2,3,4-trimethoxybenzene

To a solution of 2,3,4-trimethoxybenzenesulfonyl chloride (500 mg, 1.88 mmol) in methanol (10 mL) is added 3-hydroxy-4-methoxyaniline (523 mg, 3.76 mmol) at ambient temperature. The reaction is stirred for 1 h, the solvent is then evaporated and the crude product is purified by flash chromatography over silica.

Example 3
Assessment of Biological Activity

Compounds can be evaluated for their ability to inhibit in vitro the growth of HeLa cells, an immortal cell line derived from a human cervical carcinoma commonly used to evaluate the cytotoxicity of potential therapeutic agents. The following data reflect the cytotoxicity of selected examples of the present invention. The values given represent the concentration of test compound required to inhibit by 50% the uptake of Alamar Blue (Biosource International, Camarillo, Calif.) by HeLa cell cultures, which correlates directly with the overall levels of cellular metabolism in the culture, and is generally accepted as an appropriate marker of cell growth. The test was conducted according to the method of Ahmed et al. (*J. Immunol. Methods* 1994, 170, 211). The following selected example displays potent cytotoxic activity in this assay, with IC$_{50}$ values ranging from 0.05 μM to 5.0 μM. Compounds were similarly evaluated for cell growth inhibition using MCF-7 cells and MCF-7/ADR cells.

| Compound | IC50 (μM) | | |
| --- | --- | --- | --- |
|  | HeLa | MCF-7 | MCF-7/ADR |
| Example 1 | 0.15 | 0.15 | 0.5 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

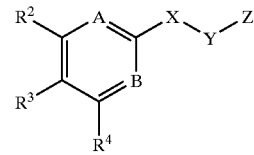

wherein,
A is C—R$^1$;
B is N;
wherein R$^1$ is selected from the group consisting of hydrogen, halogen, (C$_1$–C$_8$)alkyl, (C$_1$–C$_8$)heteroalkyl, —OR$^6$, —NR$^6$R$^7$, —S(O)$_m$R$^6$, —CN, —NO$_2$, —S(O)$_n$NR$^6$R$^7$, and —N$_3$, wherein R$^6$ and R$^7$ are independently selected from hydrogen, (C$_1$–C$_8$)alkyl, and (C$_1$–C$_8$)heteroalkyl; subscript m is an integer of from 0 to 3; and subscript n is an integer of from 1 to 2;
R$^2$ and R$^3$ are members independently selected from the group consisting of —OR$^8$, —SR$^8$ and —NR$^8$R$^9$, wherein R$^8$ and R$^9$ are independently selected from the group consisting of hydrogen, (C$_1$–C$_6$)alkyl and (C$_1$–C$_6$)heteroalkyl;
R$^4$ is a member selected from the group consisting of hydrogen, (C$_1$–C$_8$)alkyl, (C$_1$–C$_8$)heteroalkyl, —OR$^{10}$, —SR$^{10}$ and —NR$^{10}$R$^{11}$, wherein R$^{10}$ and R$^{11}$ are independently selected from the group consisting of hydrogen, (C$_1$–C$_6$)alkyl and (C$_1$–C$_6$)heteroalkyl; and optionally, R$^1$ is linked to R$^2$ to form a fused ring, R$^2$ is linked to R$^3$ to form a fused ring, or R$^2$ is linked to both of R$^1$ and R$^3$ to form two additional fused rings;
X is a member selected from the group consisting of —S(O)$_p$— and —C(O)—, wherein subscript p is 1 or 2;
Y is a member selected from the group consisting of a single bond, —CH$_2$— and —N(R$^{12}$)—, wherein R$^{12}$ is selected from the group consisting of hydrogen, (C$_1$–C$_6$)alkyl, (C$_1$–C$_6$)heteroalkyl and arylalkyl; and
Z is a member selected from the group consisting of aryl and arylalkyl, optionally having from 1 to 5 substituents independently selected from the group consisting of halogen, $(C_1-C_8)$alkyl, $(C_1-C_8)$heteroalkyl, —CN, —NO$_2$, —OR', —SR', —OC(O)NR'R", NR"C(O)R', —NR"C(O)$_2$R', —NH—C(NH$_2$)=NH, —NR'C(NH$_2$)=NH, —NH—C(NH$_2$)=NR', —NR'R", perfluoro $(C_1-C_8)$alkoxy, and perfluoro$(C_1-C_8)$alkyl, wherein R' and R" are independently selected from the group consisting of hydrogen, $(C_1-C_8)$alkyl, and $(C_1-C_8)$heteroalkyl.

2. A compound of claim 1, wherein $R^1$ is linked to $R^2$ to form a 5- or 6-membered ring.

3. A compound of claim 1, wherein $R^2$ is linked to $R^3$ to form a 5- or 6-membered ring.

4. A composition comprising a pharmaceutically acceptable excipient and a compound having the formula:

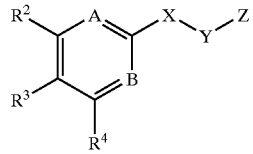

wherein,
A is C—$R^1$;
B is N;
wherein $R^1$ is selected from the group consisting of hydrogen, halogen, $(C_1-C_8)$alkyl, $(C_1-C_8)$heteroalkyl, —OR, —NR$^6$R$^7$, —S(O)$_m$R$^6$, —CN, —NO$_2$, —S(O)$_n$NR$^6$R$^7$, and —N$_3$, wherein $R^6$ and $R^7$ are independently selected from hydrogen, $(C_1-C_8)$alkyl, and $(C_1-C_8)$heteroalkyl; subscript m is an integer of from 0 to 3; and subscript n is an integer of from 1 to 2;
$R^2$ and $R^3$ are members independently selected from the group consisting of —OR$^8$, —SR$^8$ and —NR$^8$R$^9$, wherein $R^8$ and $R^9$ are independently selected from the group consisting of hydrogen, $(C_1-C_6)$alkyl and $(C_1-C_6)$heteroalkyl;
$R^4$ is a member selected from the group consisting of hydrogen, $(C_1-C_8)$alkyl, $(C_1-C_8)$heteroalkyl, —OR$^{10}$, —SR$^{10}$ and —NR$^{10}$R$^{11}$, wherein $R^{10}$ and $R^{11}$ are independently selected from the group consisting of hydrogen, $(C_1-C_6)$alkyl and $(C_1-C_6)$heteroalkyl; and optionally, $R^1$ is linked to $R^2$ to form a fused ring, $R^2$ is linked to $R^3$ to form a fused ring, or $R^2$ is linked to both of $R^1$ and $R^3$ to form two additional fused rings;
X is a member selected from the group consisting of —S(O)$_p$— and —C(O)—, wherein subscript p is 1 or 2;
Y is a member selected from the group consisting of a single bond, —CH$_2$— and —N(R$^{12}$)—, wherein R$^{12}$ is selected from the group consisting of hydrogen, $(C_1-C_6)$alkyl, $(C_1-C_6)$heteroalkyl and arylalkyl; and
Z is a member selected from the group consisting of aryl and arylalkyl, optionally having from 1 to 5 substituents independently selected from the group consisting of halogen, $(C_1-C_8)$alkyl, $(C_1-C_8)$heteroalkyl, —CN, —NO$_2$, —OR', —SR', —OC(O)NR'R", NR"C(O)R', —NR"C(O)$_2$R', —NH—C(NH$_2$)=NH, —NR'C(NH$_2$)=NH, —NH—C(NH$_2$)=NR', —NR'R", perfluoro $(C_1-C_8)$alkoxy, and perfluoro$(C_1-C_8)$alkyl, wherein R' and R" are independently selected from the group consisting of hydrogen, $(C_1-C_8)$alkyl, and $(C_1-C_8)$heteroalkyl.

5. A composition of claim 4, wherein $R^1$ is linked to $R^2$ to form a 5- or 6-membered ring.

6. A composition of claim 4, wherein $R^2$ is linked to $R^3$ to form a 5- or 6-membered ring.

7. A method for treating or preventing a disease state characterized by abnormally high levels of low density lipoprotein particles or cholesterol in the blood, or by an abnormally high level of cell proliferation, which method comprises administering to a mammalian subject in need thereof a therapeutically effective amount of a composition containing a compound having the formula:

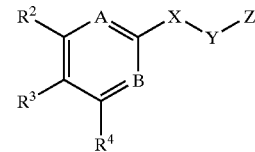

wherein,
A is C—$R^1$;
B is N;
wherein $R^1$ is selected from the group consisting of hydrogen, halogen, $(C_1-C_8)$alkyl, $(C_1-C_8)$heteroalkyl, —OR$^6$, —NR$^6$R$^7$, —S(O)$_m$R$^6$, —CN, —NO$_2$, —S(O)$_n$N$^6$R$^7$, and —N$_3$, wherein $R^6$ and $R^7$ are independently selected from hydrogen, $(C_1-C_8)$alkyl, and $(C_1-C_8)$heteroalkyl; subscript m is an integer of from 0 to 3; and subscript n is an integer of from 1 to 2;
$R^2$ and $R^3$ are members independently selected from the group consisting of —OR$^8$, —SR$^8$ and —NR$^8$R$^9$, wherein $R^8$ and $R^9$ are independently selected from the group consisting of hydrogen, $(C_1-C_6)$alkyl and $(C_1-C_6)$heteroalkyl;
$R^4$ is a member selected from the group consisting of hydrogen, $(C_1-C_8)$alkyl, $(C_1-C_8)$heteroalkyl, —OR$^{10}$, —SR$^{10}$ and —NR$^{10}$R$^{11}$, wherein $R^{10}$ and $R^{11}$ are independently selected from the group consisting of hydrogen, $(C_1-C_6)$alkyl and $(C_1-C_6)$heteroalkyl; and optionally, $R^1$ is linked to $R^2$ to form a fused ring, $R^2$ is linked to $R^3$ to form a fused ring, or $R^2$ is linked to both of $R^1$ and $R^3$ to form two additional fused rings;
X is a member selected from the group consisting of —S(O)$_p$— and —C(O)—, wherein subscript p is 1 or 2;
Y is a member selected from the group consisting of a single bond, —CH$_2$— and —N(R$^{12}$)—, wherein R$^{12}$ is selected from the group consisting of hydrogen, $(C_1-C_6)$alkyl, $(C_1-C_6)$heteroalkyl and arylalkyl; and
Z is a member selected from the group consisting of aryl and arylalkyl, optionally having from 1 to 5 substituents independently selected from the group consisting of halogen, $(C_1-C_8)$alkyl, $(C_1-C_8)$heteroalkyl, —CN, —NO$_2$, —OR', —SR', —OC(O)NR'R", NR"C(O)R', —NR"C(O)$_2$R', —NH—C(NH$_2$)=NH, —NR'C(NH$_2$)=NH, —NH—C(NH$_2$)=NR', —NR'R", perfluoro $(C_1-C_8)$alkoxy, and perfluoro$(C_1-C_8)$alkyl, wherein R' and R" are independently selected from the group consisting of hydrogen, $(C_1-C_8)$alkyl, and $(C_1-C_8)$heteroalkyl.

8. A method in accordance with claim 7, wherein $R^1$ is linked to $R^2$ to form a 5- or 6-membered ring.

9. A method in accordance with claim 7, wherein $R^2$ is linked to $R^3$ to form a 5- or 6-membered ring.

10. A compound of claim 1, wherein A is C—$R^1$, X is —S(O)$_2$—, Y is —N(R$^{12}$)—, Z is a substituted or unsubstituted phenyl group, and $R^1$ and $R^5$ are independently selected from the group consisting of hydrogen and $(C_1-C_3)$alkyl.

11. A compound of claim 1, wherein A is C—R¹, X is —S(O)₂—, Y is —NH—, and Z is a substituted phenyl group.

12. A compound of claim 1, wherein A is C—H, R² is —OR⁸, R³ is —OR⁸, X is —S(O)₂—, Y is —NH—, and Z is a substituted phenyl group.

13. A compound of claim 1, wherein A is C—H, R² is —OR⁸, R³ is —OR⁸, R⁴ is hydrogen or —OR¹⁰, X is —S(O)₂—, Y is —NH—, and Z is a substituted phenyl group.

14. A compound of claim 1, wherein A is C—H, R² is —OR⁸, R³ is —OR⁸, R⁴ is —OR¹⁰, X is —S(O)₂—, Y is —N(R¹²)—, and Z is a substituted phenyl group represented by:

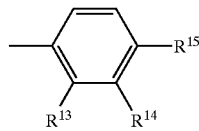

wherein R¹³, R¹⁴ and R¹⁵ are each independently selected from the group consisting of hydrogen, halogen, (C₁–C₆) alkyl, (C₁–C₆)heteroalkyl, —OR¹⁶, —NR¹⁶R¹⁷, —CN, —NO₂, wherein R¹⁶ and R¹⁷ are independently selected from hydrogen, (C₁–C₆)alkyl and (C₁–C₆)heteroalkyl.

15. A compound of claim 1, wherein A is C—H, R² is —OR⁸, R³ is —OR⁸, R⁴ is —OR¹⁰, X is —S(O)₂—, Y is —NH—, and Z is a substituted phenyl group represented by:

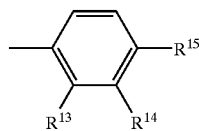

wherein R¹³, R¹⁴ and R¹⁵ are each independently selected from the group consisting of hydrogen, halogen, (C₁–C₆) alkyl, (C₁–C₆)heteroalkyl, —OR¹⁶, —NR¹⁶R¹⁷, —CN, —NO₂, wherein R¹⁶ and R¹⁷ are independently selected from hydrogen, (C₁–C₆)alkyl and (C₁–C₆)heteroalkyl.

16. A compound of claim 14, wherein R¹³ is hydrogen and R⁴¹ and R¹⁵ are other than hydrogen.

17. A compound of claim 15, wherein R¹³ is hydrogen and R¹⁴ and R¹⁵ are other than hydrogen.

18. A compound of claim 1, wherein A is C—H, R² and R³ are independently selected from the group consisting of methoxy, difluoromethoxy and trifluoromethoxy, R⁴ is a member selected from the group consisting of hydrogen, methoxy, difluoromethoxy and trifluoromethoxy, X is —S(O)₂—, Y is —NH—, and Z is phenyl substituted by one or more fluoro, methoxy, or hydroxy groups.

19. A compound of claim 1, wherein A is C—H, R² and R³ are independently selected from the group consisting of methoxy, difluoromethoxy and trifluoromethoxy, R⁴ is a member selected from the group consisting of hydrogen, methoxy, difluoromethoxy and trifluoromethoxy, X is —S(O)₂—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

20. A compound of claim 1, wherein A is C—H, R², R³ and R⁴ are each methoxy, X is —S(O)₂—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

21. A compound of claim 1, wherein A is C—OCH₃, R² and R³ are each methoxy, R⁴ is hydrogen, X is —S(O)₂—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

22. A composition of claim 4, wherein A is C—R¹, X is —S(O)₂—, Y is —N(R¹²)—, Z is a substituted or unsubstituted phenyl group, and R¹ and R⁵ are independently selected from the group consisting of hydrogen and (C₁–C₃) alkyl.

23. A composition of claim 4, wherein A is C—R¹, X is —S(O)₂—, Y is —NH—, and Z is a substituted phenyl group.

24. A composition of claim 4, wherein A is C—H, R² is —OR⁸, R³ is —OR⁸, X is —S(O)₂—, Y is —NH—, and Z is a substituted phenyl group.

25. A composition of claim 4, wherein A is C—H, R² is —OR⁸, R³ is —OR⁸, R⁴ is hydrogen or —OR¹⁰, X is —S(O)₂—, Y is —NH—, and Z is a substituted phenyl group.

26. A composition of claim 4, wherein A is C—H, R² is —OR⁸, R³ is —OR⁸, R⁴ is —OR¹⁰, X is —S(O)₂—, Y is —N(R¹²)—, and Z is a substituted phenyl group represented by:

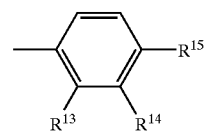

wherein R¹³, R¹⁴ and R¹⁵ are each independently selected from the group consisting of hydrogen, halogen, (C₁–C₆) alkyl, (C₁–C₆)heteroalkyl, —OR¹⁶, —NR¹⁶R¹⁷, —CN, —NO₂, wherein R¹⁶ and R¹⁷ are independently selected from hydrogen, (C₁–C₆)alkyl and (C₁–C₆)heteroalkyl.

27. A composition of claim 4, wherein A is C—H, R² is —OR⁸, R⁸, R³ is —OR⁸, R⁴ is —OR¹⁰, X is —S(O)₂—, Y is —NH—, and Z is a substituted phenyl group represented by:

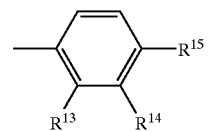

wherein R¹³, R¹⁴ and R¹⁵ are each independently selected from the group consisting of hydrogen, halogen, (C₁–C₆) alkyl, (C₁–C₆)heteroalkyl, —OR¹⁶, —NR¹⁶R¹⁷, —CN, —NO₂, wherein R¹⁶ and R¹⁷ are independently selected from hydrogen, (C₁–C₆)alkyl and (C₁–C₆)heteroalkyl.

28. A composition of claim 26, wherein R¹³ is hydrogen and R¹⁴ and R¹⁵ are other than hydrogen.

29. A composition of claim 27, wherein R¹³ is hydrogen and R¹⁴ and R¹⁵ are other than hydrogen.

30. A composition of claim 4, wherein A is C—H, R² and R³ are independently selected from the group consisting of methoxy, difluoromethoxy and trifluoromethoxy, R⁴ is a member selected from the group consisting of hydrogen, methoxy, difluoromethoxy and trifluoromethoxy, X is —S(O)₂—, Y is —NH—, and Z is phenyl substituted by one or more fluoro, methoxy, or hydroxy groups.

31. A composition of claim 4, wherein A is C—H, R² and R³ are independently selected from the group consisting of methoxy, difluoromethoxy and trifluoromethoxy, R⁴ is a member selected from the group consisting of hydrogen, methoxy, difluoromethoxy and trifluoromethoxy, X is —S(O)$_2$—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

32. A composition of claim 4, wherein A is C—H, R$^2$, R$^3$ and R$^4$ are each methoxy, X is —S(O)$_2$—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

33. A composition of claim 4, wherein A is C—OCH$_3$, R$^2$ and R$^3$ are each methoxy, R$^4$ is hydrogen, X is —S(O)$_2$—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

34. A method in accordance with claim 7, wherein A is C—R$^1$, X is —S(O)$_2$—, Y is —N(R$^{12}$)—, Z is a substituted or unsubstituted phenyl group, and R$^1$ and R$^5$ are independently selected from the group consisting of hydrogen and (C$_1$–C$_3$)alkyl.

35. A method in accordance with claim 7, wherein A is C—R$^1$, X is —S(O)$_2$—, Y is —NH—, and Z is a substituted phenyl group.

36. A method in accordance with claim 7, wherein A is C—H, R$^2$ is —OR$^8$, R$^3$ is —OR$^8$, X is —S(O)$_2$—, Y is —NH—, and Z is a substituted phenyl group.

37. A method in accordance with claim 7, wherein A is C—H, R$^2$ is —OR$^8$, R$^3$ is —OR$^8$, R$^4$ is hydrogen or —OR$^{10}$, X is —S(O)$_2$—, Y is —NH—, and Z is a substituted phenyl group.

38. A method in accordance with claim 7, wherein A is C—H, R$^2$ is —OR$^8$, R$^3$ is —OR$^8$, R$^4$ is —OR$^{10}$, X is —S(O)$_2$—, Y is —N(R$^{12}$)—, and Z is a substituted phenyl group represented by:

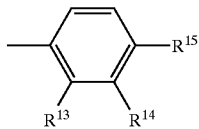

wherein R$^{13}$, R$^{14}$ and R$^{15}$ are each independently selected from the group consisting of hydrogen, halogen, (C$_1$–C$_6$) alkyl, (C$_1$–C$_6$)heteroalkyl, —OR$^{16}$, —NR$^{16}$R$^{17}$, —CN, —NO$_2$, wherein R$^{16}$ and R$^{17}$ are independently selected from hydrogen, (C$_1$–C$_6$)alkyl and (C$_1$–C$_6$)heteroalkyl.

39. A method in accordance with claim 7, wherein A is C—H, R$^2$ is —OR$^8$, R$^3$ is —OR$^8$, R$^4$ is —OR$^{10}$, X is —S(O)$_2$—, Y is —NH—, and Z is a substituted phenyl group represented by:

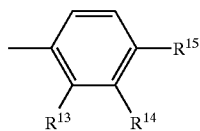

wherein R$^{13}$, R$^{14}$ and R$^{15}$ are each independently selected from the group consisting of hydrogen, halogen, (C$_1$–C$_6$) alkyl, (C$_1$–C$_6$)heteroalkyl, —OR$^{16}$, —NR$^{16}$R$^{17}$, —CN, —NO$_2$, wherein R$^{16}$ and R$^{17}$ are independently selected from hydrogen, (C$_1$–C$_6$)alkyl and (C$_1$–C$_6$)heteroalkyl.

40. A method in accordance with claim 38, wherein R$^{13}$ is hydrogen and R$^{14}$ and R$^{15}$ are other than hydrogen.

41. A method in accordance with claim 39, wherein R$^{13}$ is hydrogen and R$^{14}$ and R$^{15}$ are other than hydrogen.

42. A method in accordance with claim 7, wherein A is C—H, R$^2$ and R$^3$ are independently selected from the group consisting of methoxy, difluoromethoxy and trifluoromethoxy, R$^4$ is a member selected from the group consisting of hydrogen, methoxy, difluoromethoxy and trifluoromethoxy, X is —S(O)$_2$—, Y is —NH—, and Z is phenyl substituted by one or more fluoro, methoxy, or hydroxy groups.

43. A method in accordance with claim 7, wherein A is C—H, R$^2$ and R$^3$ are independently selected from the group consisting of methoxy, difluoromethoxy and trifluoromethoxy, R$^4$ is a member selected from the group consisting of hydrogen, methoxy, difluoromethoxy and trifluoromethoxy, X is —S(O)$_2$—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

44. A method in accordance with claim 7, wherein A is C—H, R$^2$, R$^3$ and R$^4$ are each methoxy, X is —S(O)$_2$—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

45. A method in accordance with claim 7, wherein A is C—OCH$_3$, R$^2$ and R$^3$ are each methoxy, R$^4$ is hydrogen, X is —S(O)$_2$—, Y is —NH—, and Z is selected from the group consisting of 4-dimethylaminophenyl, 4-aminophenyl, 4-methoxyphenyl, 3-fluoro-4-methoxyphenyl and 3-hydroxy-4-methoxyphenyl.

46. A method in accordance with claim 7, wherein said compound in administered parenterally.

47. A method in accordance with claim 7, wherein said compound is administered topically.

48. A method in accordance with claim 7, wherein said compound in administered orally.

49. A method in accordance with claim 7, wherein said disease state is selected from the group consisting of atherosclerosis, pancreatitis, psoriasis and inflammatory diseases states.

50. A method in accordance with claim 7, wherein said disease state is cancer.

* * * * *